United States Patent [19]

McCoy et al.

[11] 3,989,755

[45] Nov. 2, 1976

[54] PRODUCTION OF OXIMES BY THE REACTION OF CARBON MONOXIDE WITH NITROCOMPOUNDS

[75] Inventors: John J. McCoy, Media; John G. Zajacek, Strafford, both of Pa.; Karl E. Fuger, Therwil, Switzerland

[73] Assignee: Atlantic Richfield Company, Los Angeles, Calif.

[22] Filed: Feb. 20, 1975

[21] Appl. No.: 551,487

Related U.S. Application Data

[63] Continuation-in-part of Ser. No. 372,457, June 21, 1973, abandoned.

[52] U.S. Cl. .................... 260/566 A; 260/586 C; 260/586 R; 260/593 R
[51] Int. Cl.² ............................... C07C 131/04
[58] Field of Search ........ 260/566 A, 586 A, 586 R, 260/593 R

[56] References Cited

UNITED STATES PATENTS

| | | | |
|---|---|---|---|
| 2,945,065 | 7/1960 | Donaruma | 260/566 A |
| 3,480,672 | 11/1969 | Kober et al. | 260/566 A |
| 3,734,964 | 5/1973 | Knifton | 260/566 A |

Primary Examiner—Gerald A. Schwartz
Attorney, Agent, or Firm—Delbert E. McCaslin

[57] ABSTRACT

Production of oximes (and ketones) by contacting at elevated temperatures and pressures, a primary or secondary saturated aliphatic nitrocompound with carbon monoxide in the presence of a catalyst comprising metallic selenium or inorganic selenium compounds and a base.

20 Claims, No Drawings

PRODUCTION OF OXIMES BY THE REACTION OF CARBON MONOXIDE WITH NITROCOMPOUNDS

RELATED APPLICATION

This application is a continuation-in-part of application Ser. No. 372,457 filed June 21, 1973, entitled PRODUCTION OF OXIMES BY THE REACTION OF CARBON MONOXIDE WITH NITROCOMPOUNDS now abandoned.

FIELD OF INVENTION

The present invention relates to a process for the manufacture of oximes (and ketones) by the reaction of carbon monoxide with a primary or secondary saturated aliphatic nitrocompound, or a saturated cycloaliphatic nitrocompound under elevated temperature and pressure conditions in the presence of a catalyst and a base.

Oximes are an important class of organic compounds and are of significant importance in industrial chemistry. Cyclohexanone oxime, for example is used as an intermediate in the manufacture of caprolactam, an important fiber precursor, by the Beckmann rearrangement. Other oximes, such as acetoxime, can be used as a source of the oxime moiety, instead of using hydroxylamine itself. This can overcome the many disadvantages in handling hydroxylamine solutions, and in the subsequent workup of its reaction mixtures. Other open chain oximes such as methyl ethyl ketoxime, butyraldoxime, etc. are used commercially as anti-skinning agents in paints.

Although methods are available for the reduction of aliphatic nitrocompounds to oximes, they have a number of disadvantages not found in the instant process. For example, in U.S. Pat. No. 3,480,672 there is described a process for the reduction of aliphatic nitrocompounds using carbonyl sulfide as a reducing agent. This process requires the use of a large molar excess of toxic carbonyl sulfide as compared to the starting nitrocompound, gives a relatively low conversion for the quantity of carbonyl sulfide used and, apparently, is not a catalytic reaction. In U.S. Pat. No. 2,945,065 there is described a method by which nitrocyclohexane is reduced to the oxime by reaction with carbon monoxide at an elevated temperature and pressure. However, this process requires that the nitrocyclohexane be converted to an alkaline nitronate salt in a previous and separate step. Further, this process requires the use of anhydrous conditions, an alkanol as a solvent (some of which is also consumed as a reactant), and a higher temperature to achieve a convenient reaction rate than is required by the instant process. In U.S. Pat. No. 3,734,964 there is described a method for partial reduction of a nitroparaffin to the corresponding oxime using critical ratios of a copper salt catalyst, nitrogenous base and water. This process requires that a base-copper catalyst complex be formed and then passing carbon monoxide into a reaction mixture of the formed complex and nitroparaffin. Other methods, well known in the art, employing hydrogen as a reducing agent are complicated by the undesirable reduction of the oxime to an amine.

SUMMARY OF THE INVENTION

In accordance with this invention a primary or secondary saturated aliphatic nitrocompound or saturated cycloaliphatic nitrocompound is contacted with carbon monoxide at temperatures in the range of from 50° to 200° C. under pressures in the range of from 10 atmospheres to 200 atmospheres in the presence of a selenium catalyst and a base.

It is an object of the present invention, therefore, to provide an improved process for the production of oximes.

It is another object of this invention to provide a process for the production of oximes and ketones.

It is another object of this invention to provide an efficient process for the production of oximes that minimizes the formation of undesirable by-products.

It is another object of this invention to provide an efficient, high yield process for the production of an efficient, high yield process for the production of oximes from the reaction of primary or secondary saturated aliphatic nitrocompounds, or a saturated cycloaliphatic nitrocompound by using metallic selenium, or inorganic compounds of selenium or combinations thereof as a catalyst in conjunction with a base.

It is another object of this invention to provide a process for the production of oximes which uses readily available, low cost starting materials.

These and other objects of the invention will become apparent from the following description of the process and from the claims.

DESCRIPTION OF THE PROCESS

In the instant process the nitrocompound is, in general, largely converted to the oxime. In some cases, however, depending on the starting nitrocompound and the particular reaction conditions employed, the corresponding ketone can be formed. For example, when nitrocyclohexane is reacted under the conditions of this process to prepare cyclohexanone oxime, cyclohexanone can be formed as a by-product. This ketone can be easily converted to the oxime by reaction with hydroxylamine or, if desired, simply separated from the cyclohexanone oxime by any number of suitable separation techniques.

Suitable nitrocompounds for the process of this invention are primary or secondary saturated aliphatic mononitrocompounds and saturated cycloaliphatic mono-nitrocompounds. The term "saturated" herein refers to compounds which contain no olefinic or acetylinic bonds but does not exclude the arylalkyl nitrocompounds. Substituted or unsubstituted nitroalkanes which are suitable include nitromethane, nitroethane, 1-nitropropane, 2-nitropropane, 1-nitrobutane, 2-nitrobutane, 1-nitropentane, 1-nitro-1-methylpropane, 1-nitro-3-methylpropane, 2-nitro-3-ethylbutane, 1-nitro-2,2-dimethylbutane, 1-nitro-3-methylbutane, 2-nitro-4-methylpentane, 1-nitrohexane, 3-nitro-4,5-dimethylhexane, 3-nitrododecane, nitrooctadecane, 5-nitro-7,8-dimethyloctadecane, and the like. Also suitable are the nitrocycloalkanes such as nitrocyclobutane, nitrocyclopentane, nitrocyclohexane, nitrocycloheptane, nitrocyclooctane, nitrocyclododecane and the like including the alkyl substituted or halo substituted compounds. Likewise the aryl nitroalkyl compounds such as phenyl nitromethane, p-bromo-phenyl nitromethand, p-toluyl nitromethane and the like are suitable. These are merely representative of the compounds suitable, since in general any nitrocompound of the types described containing up to 20 carbon atoms can be employed including mixtures of such nitrocompounds.

Catalysts for use in this invention include selenium. In addition, various compounds containing selenium can be used alone or in combination with selenium metal. One of the simpletst and least expensive forms of selenium is the metal itself which can be as good, if not better, than most selenium compounds. Nevertheless, good yields can be obtained with such compounds as selenium dioxide, titanium diselenide, sodium selenite, zinc selenite, zinc selenide, tungsten selenide, selenium sulfide and selenium disulfide.

The catalyst material, as indicated above, can be self-supported or the catalyst material can be deposited on a support or carrier for dispersing the catalyst to increase its effective surface. Alumina, silica, carbon, asbestos, bentonite, diatomaceous earth, fuller's earth, and analogous materials are useful as carriers for this purpose. Preferably, the carrier selected is one which is inert in the described process.

A base must also be added to the reaction. Organic bases, metal salts of carboxylic acids and metal hydroxides have been found to be effective. Organic bases suitable for the reaction are tertiary amines such as triethylamine, pyridine, quinoline and N,N-dimethylaniline. Other amines, such as secondary amines, exemplified by diethylamine are also suitable. Thus, aliphatic, aliphaticaromatic and aromatic heterocyclic amines can be employed in this reaction. Not all amines of the group described are equivalent to one another in their ability to affect high yields of oximes. In general, those amines which are stronger bases give higher yields than those which are classed as weak bases. Thus, triethylamine is preferred over pyridine as an organic base. It is important to note, however, that the choice of base and base strength used to affect high yields of oximes is dependent on the starting nitrocompound. There are examples in which a base not strongly effective for one nitrocompound can prove very effective for another nitrocompound.

Compounds normally considered as weak bases, such as the metal salts of carboxylic acids, can also be employed to good advantage. Examples of such compounds are lithium acetate, sodium acetate, potassium acetate, calcium acetate, sodium formate, lithium formate and antimony triacetate. The acid salts can be added preformed or can be generated "in situ" by adding appropriate quantities of the corresponding acid and base. There is no limit on the type of acid used or the corresponding metal oxide or hydroxide employed. If desired, metal hydroxides or oxides, themselves, can be used as bases.

While the process of the invention can typically be operated effectively in the absence of a solvent, a solvent can be employed. Use of a suitable solvent such as benzene, toluene, xylene, aliphatic halogenated hydrocarbons, halogenated aromatic hydrocarbons can be used. In addition, ether solvents such as tetrahydrofuran, 1,4-dioxane, 1,2-dimethoxyethane and the like are effective. Alcohols can also be used as solvents such as methanol, ethanol, isopropanol and tert-butanol. A particularly advantageous and preferred solvent is one of the tertiary amines previously described. Such a solvent can also act as the necessary base.

Combinations of an amine solvent such as pyridine with an additional amine base such as triethylamine can be particularly effective for certain nitrocompounds, while with other compounds such a combination offers no distinct advantage and a solvent such as pyridine is also suitable as the base.

It will be understood from the foregoing disclosure that all of the disclosed catalysts, solvents and bases are operable with all of the nitrocompounds disclosed for the production of the oximes. It will be distinctly understood, however, by those skilled in this art that every combination is not equally effective in maximizing oxime production from a particular nitrocompound starting material since these vary widely in their reactivity.

The catalyst of this invention is preferably used in molar ratios of 2:1 to 1000:1 of the nitrocompound to catalyst. Preferably, the molar amounts of the nitrocompound to catalyst is in the range of from 5:1 to 100:1. It will be understood, however, that larger or smaller amounts of catalyst can be used. The ratio of base to nitrocompound can range from 0.01:1 to 10:1, however, larger or smaller amounts can be used, for example, when an amine is used as both solvent and base the quantity of base is of necessity far in excess of the molar quantity of the catalyst or of nitrocompound since it must be and is sufficient to dissolve the nitrocompound.

The order of mixing the reactants is not critical and can be varied within the limitations of the equipment employed. A simple procedure is to charge the nitrocompound, the solvent, catalyst and base in the desired quantities into the reaction vessel, introduce the proper amount of carbon monoxide and then heat the mixture to obtain the desired reaction. A suitable pressure vessel, such as an autoclave, which is preferably provided with heating means and agitation means, such as a stirrer or an external rocking mechanism, is employed for the reaction.

Generally, the amount of carbon monoxide in the free space of the reactor is sufficient to maintain the desired pressure, as well as to provide a reactant for the process. As the reaction progresses, additional carbon monoxide can be fed to the reactor either intermittenly or continuously. Although greater and lesser amounts of carbon monoxide can be employed if desired, generally the total amount of carbon monoxide added during the reaction is between about 3 moles and about 50 moles and preferably between about 5 moles and about 15 moles of carbon monoxide per mole of nitrocompound.

The reaction temperature is generally maintained in the range of from 50° to 200° C. and preferably within the range of from 80° to 150° C. These temperature ranges permit a convenient rate of reaction to be achieved, while avoiding undesirable side reactions. It will be understood, however, that any elevated temperatures below that at which the starting materials or the products decompose can be used. The reaction is carried out, as indicated above, at superatmospheric pressures which is normally between about 10 and about 200 atmospheres, although higher or lower reaction pressures can be employed if other reaction conditions are suitably adjusted. Preferably, however, only moderate carbon monoxide pressures in the range of about 10 to about 60 atmospheres are employed and the reaction is conveniently run at a temperature of below about 150° C. within this pressure range.

While the reaction of the present invention is normally carried out batchwise, if desired, the reaction can be carried out semi-continuously or even continuously. The reaction time is dependent upon the nature of the reactants, temperature, pressure and the type of catalyst employed, as well as the type of equipment which is used. In general, however, reaction times ranging from 0.25 to 4.0 hours can be used. The shorter times with the more active catalysts, more reactive nitrocompounds or more severe reaction conditions, while the longer times are associated with less active catalysts, the less reactive nitrocompounds, and the less severe reaction conditions. For most reactions, times from 0.5 to 2.0 hours can be used.

After the reaction has been completed, the temperature of the reaction mixture can be dropped to room temperature and the pressure vessel vented. The reaction product is then treated by conventional procedures, including filtration, distillation, or other suitable separation techniques, to effect separation of the oxime from unreacted starting material, solvent, by-product, catalyst and other material which may be present.

The following examples set forth in tabular form the conditions and results obtained in a series of typical runs. These are not to be construed as limiting the invention solely to their disclosure.

EXAMPLE I

Each run was carried out in a 300 ml. capacity 316 Stainless Steel rocking autoclave. The conditions (except where noted otherwise) were: 0.5 g. selenium (metallic powder); initial charge of 800 psig carbon monoxide; 5.0 g nitro-cyclohexane; reaction temperature, 130° C.; time, 1 hour. The results and remarks are shown in Table I. The ketone produced was cyclohexanone and the oxime produced was cyclohexanone oxime.

TABLE I

| Run No. | Solvent ml | Base g | Mole % Conv.[1] | Mole % Sel.[2] to Ketone | Mole % Sel.[2] to Oxime | Remarks |
|---|---|---|---|---|---|---|
| 1 | Pyridine 75 | TEA[3] 3.6 g | 3.1 | — | — | No selenium, comparative run. |
| 2 | Tetrahydrofuran 75 | TEA 3.6 g | 39.2 | 5.2 | 38.8 | Shows use of ether solvent with amine base. |
| 3 | Ethyl Alcohol 75 | TEA 3.6 g | 76.7 | 8.7 | 26.9 | Alcohol solvent with amine base. |
| 4 | Pyridine 75 | TEA 3.6 g | 78.5 | 4.2 | 42.4 | Combination pyridine solvent with amine base — best conversion and yield among these runs. |
| 5 | Pyridine 75 | TEA 3.6 g | 64.3 | — | 47.4 | ½ hour run. |
| 6 | Pyridine 75 | — | 17.3 | 14.9 | 41.8 | Low conversion shows pyridine is not preferable as both base and solvent with nitrocyclohexane. |
| 7 | Pyridine 75 | — | 23.1 | 5.0 | 25.0 | Temp. 170°; higher temperature do not improve pyridine as both solvent and base. |
| 8 | $CH_3OH$ 75 | TEA 0.72 g | 24.3 | — | 9.5 | Reaction temp. 70° C. |
| 9 | $CH_3OH$ 75 | TEA[3] 0.72 g | 78.0 | 44.0 | 22.5 | Reaction temp. 100° C. — higher yield of ketone with $CH_3OH$ solvent. |
| 10 | Pyridine 75 | TEA 0.72 g | 58.6 | — | 17.6 | Reaction temp. = 100° C. |
| 11 | $CH_3OH$ 75 | KOH[4] 1.0 g | 100.0 | 45.2 | — | No oxime with this solvent — base combination. |
| 12 | $CH_3OH$ 75 | KOAc . $H_2O$[5] 1.0 g | 88.8 | 31.4 | 5.8 | Low oxime yield with $CH_3OH$ again. |
| 13 | Pyridine 75 | KOH 1.0 g | 70.5 | 27.1 | 39.1 | Pyridine — KOH — higher yield of oxime. |
| 14 | Pyridine 75 | TEA 1.45 g | 70.5 | — | 23.4 | Increasing amount of TEA decreases conversion slightly, but greatly increases yield. |
| 15 | Pyridine 75 | TEA 7.2 g | 63.8 | 8.0 | 28.3 | Increasing amount of TEA decreases conversion slightly, but greatly increases yield. |
| 16 | Pyridine 75 | TEA[3] 18.0 g | 61.2 | — | 50.6 | Increasing amount of TEA decreases conversion slightly, but greatly increases yield. |
| 17 | Pyridine 75 | TEA 3.7 g | 58.6 | — | 30.8 | 0.1 g $H_2O$ added — decreased conversion. |
| 18 | $CH_3OH$ 75 | TEA 0.72 g | 76.7 | 40.4 | 16.8 | 0.1 g $H_2O$ added. |
| 19 | Pyridine 75 | DEA[6] 2.6 g | 56.0 | — | 15.7 | Secondary amine base. |

Footnotes:
[1]Conv. = mole per cent of nitrocompound converted.
[2]Sel. = mole per cent of ketone and oxime produced based on amount of nitrocompound converted.
[3]TEA = triethylamine.
[4]KOH = potassium hydroxide.
[5]KOAc . $H_2O$ = potassium acetate monohydrate.
[6]DEA = diethylamine.

EXAMPLE II

Two runs were carried out on 2-nitropropane giving acetoxime and acetone. The same equipment was employed as in Example I utilizing: 0.5 g selenium; initial charge of 800 psig CO; 5.0 g 2-nitropropane; reaction temperature, 150° C.; time, 1 hour. The results are shown in Table II.

TABLE II

| Run No. | Solvent ml | Base g | Mole % Conv.[1] | Mole % Sel.[2] to Ketone | Mole % Sel.[2] to Oxime | Remarks |
|---|---|---|---|---|---|---|
| 20 | Tetrahydrofuran 75 | TEA[3] 3.6 g | 40.3 | — | 86.9 | 150° C. |

TABLE II-continued

| Run No. | Solvent ml | Base g | Mole % Conv.[1] | Mole % Sel.[2] to Ketone | Mole % Sel.[2] to Oxime | Remarks |
|---|---|---|---|---|---|---|
| 21 | Pyridine 75 | — | 56.1 | 3.1 | 87.5 | 150° C. — note pyridine here adequate as the base as well as the solvent. |

Footnotes:
[1]Conv. = mole per cent of nitrocompound converted.
[2]Sel. = mole per cent of ketone and oxime produced based on amount of nitrocompound converted.
[3]TEA = triethylamine.

It will be seen from the data in the foregoing examples that methyl alcohol is not a preferred solvent for oxime production, in general, it favors the production of the ketone instead of the oxime, irrespective of the base employed. The combination of pyridine as the solvent (which is basic) with a stronger organic base such as triethylamine gives the best conversion and yield of the oxime from nitrocyclohexane with the optimum being shown in Run No. 4 as compared with Nos. 14, 15 and 16.

The amount of solvent in each of the runs shown was the same for purposes of comparison, i.e. 15 ml solvent per gram of nitrocompound, however this was merely for experimental convenience and amounts ranging from about 2 ml of solvent per gram of nitrocompound to 30 ml per gram also is a convenient range. It will be understood, however, that the amount of solvent should always be sufficient to dissolve completely the nitrocompound. Very large amounts of solvent do not have any benefit and merely add to the cost of processing.

The following examples set forth the conditions and results obtained employing various selenium compounds as the catalyst. In each example the process was carried out in a 300 ml capacity 316 Stainless Steel rocking autoclave.

EXAMPLE III

Five grams of nitrocyclohexane, 50 milliliters of pyridine, 50 milliliters of N,N-dimethylaniline and 1.0 gram selenium dioxide were charged to the autoclave. After pressuring to 800 psig with carbon monoxide it was heated to 150° C. for 1 hour. Analysis of the reaction solution by gas chromatography showed a conversion of nitrocyclohexane of 73.5 per cent with a selectivity to cyclohexanone oxime of 48 percent.

EXAMPLE IV

To the 300 milliliter autoclave were charged 5.0 grams nitrocyclohexane, 50 millileters of pyridine, 50 milliliters of triethylamine and 1.0 gram titanium diselenide. The autoclave was sealed, pressured to 1000 psig with carbon monoxide and heated to 120° C. for 1 hour. A conversion of nitrocyclohexane of 85 per cent with a selectivity to cyclohexanone oxime 54 per cent was obtained.

EXAMPLE V

Five grams of 2-nitropropane, 50 milliliters of pyridine, 50 milliliters of triethylamine and 1.0 gram selenium disulfide were charged to the autoclave. After heating for one hour at 150° C. with 1200 psig carbon monoxide a conversion of 2-nitropropane of 60 per cent with a selectivity to acetoxime of 85 per cent was obtained.

EXAMPLE VI

Fifty milliliters of tetrahydrofuran, 50 milliliters of triethylamine, 5.0 grams nitrocyclohexane and 1.5 grams sodium selenite were charged to the autoclave. After pressuring to 800 psig with carbon monoxide it was heated to 120° C. for 1 hour. A nitrocyclohexane conversion of 43 per cent was found with a selectivity to cyclohexanone oxime of 54 per cent.

EXAMPLE VII

Five grams of nitrocyclohexane, 50 milliliters of pyridine, 50 milliliters of triethylamine, 0.25 gram selenium metal and 0.31 gram selenium dioxide were charged to the autoclave. After pressuring to 800 psig with carbon monoxide it was heated to 150° C. for 1 hour. Analysis of the reaction solution by gas chromatography showed a conversion of nitrocyclohexane of 75 per cent with a selectivity to cyclohexanone oxime of 52 per cent.

We claim:

1. A method for the production of a material selected from the group consisting of an oxime, a ketone and mixtures thereof which comprises contacting a nitrocompound containing up to 20 carbon atoms selected from the group consisting of primary saturated aliphatic mono-nitrocompounds, secondary saturated aliphatic mono-nitrocompounds and saturated cycloaliphatic mono-nitrocompounds with carbon monoxide at a pressure in the range of from 10 atmospheres to 200 atmospheres, at a temperature in the range of from 50° to 200° C. in the presence of a catalyst selected from the group consisting of metallic selenium, inorganic compounds of selenium selected from selenium dioxide, titanium diselenide, sodium selenite, zinc selenite, zinc selenide, tungsten selenide, selenium sulfide or selenium disulfide, and combinations thereof and in the presence of a base selected from the group consisting of aliphatic amines, aliphatic-aromatic amines, aromatic heterocyclic amines, metals of carboxylic acids and metal hydroxides.

2. The method according to claim 1 wherein said mono-nitrocompound is a primary saturated aliphatic nitrocompound.

3. The method according to claim 1 wherein said mono-nitrocompound is a secondary saturated aliphatic nitrocompound.

4. The method according to claim 3 wherein said secondary nitrocompound is 2-nitropropane.

5. The method according to claim 1 wherein said mono-nitrocompound is a saturated cycloaliphatic nitrocompound.

6. A method according to claim 5 wherein said nitrocompound is nitrocyclohexane.

7. The method according to claim 1 wherein the pressure is in the range of from 10 atmospheres to 60 atmospheres and the temperature is in the range of from 80° to 150° C.

8. The method according to claim 1 wherein said amine base is pyridine.

9. The method according to claim 1 wherein said amine base is triethylamine.

10. The method according to claim 1 wherein said amine base is diethylamine.

11. The method of claim 1 wherein said amine base is N,N-dimethylaniline.

12. The method according to claim 1 wherein said metal salt of the carboxylic acid is potassium acetate.

13. The method according to claim 1 wherein said metal hydroxide is potassium hydroxide.

14. The method according to claim 1 wherein said mono-nitrocompound is dissolved in a solvent.

15. The method according to claim 1 wherein said catalyst is metallic selenium.

16. A method according to claim 1 wherein said catalyst is an inorganic compound of selenium.

17. A method according to claim 1 wherein said catalyst is an inorganic compound of selenium and said base is selected from the group consisting of pyridine, N,N-dimethylaniline and triethylamine.

18. A method for the production of cyclohexanone oxime and cyclohexanone which comprises contacting nitrocyclohexane with carbon monoxide at a pressure in the range of from 10 atmospheres to 200 atmospheres, at a temperature in the range of from 50° to 200° C. in the presence of a catalyst selected from the group consisting of metallic selenium, inorganic compounds of selenium selected from selenium dioxide, titanium diselenide, sodium selenite, zinc selenite, zinc selenide, tungsten selenide, selenium sulfide or selenium disulfide, and combinations thereof and in the presence of a base selected from the group consisting of aliphatic amines, aliphatic-aromatic amines, aromatic heterocyclic amines, metal salts of carboxylic acids and metal hydroxides.

19. The method according to claim 18 wherein said catalyst is metallic selenium and said base is selected from the group consisting of pyridine, triethylamine, diethylamine, potassium acetate and potassium hydroxide.

20. A method according to claim 18 wherein said catalyst is an inorganic compound of selenium selected from the group consisting of selenium dioxide, titanium diselenide and sodium selenite and said base is selected from pyridine, triethylamine or N,N-dimethylaniline.

* * * * *